United States Patent
Linares

(10) Patent No.: US 11,766,391 B2
(45) Date of Patent: Sep. 26, 2023

(54) HAIR CARE COMPOSITIONS AND METHODS OF MAKING AND USING SAME

(71) Applicant: HSP Technologies LLC, Royal Palm Beach, FL (US)

(72) Inventor: Francisco J. Linares, Coral Gables, FL (US)

( * ) Notice: Subject to any disclaimer, the term of this patent is extended or adjusted under 35 U.S.C. 154(b) by 0 days.

(21) Appl. No.: 16/417,914

(22) Filed: May 21, 2019

(65) Prior Publication Data

US 2019/0358136 A1 Nov. 28, 2019

Related U.S. Application Data

(60) Provisional application No. 62/674,736, filed on May 22, 2018.

(51) Int. Cl.

| A61K 8/34 | (2006.01) |
|---|---|
| A61K 8/41 | (2006.01) |
| A61K 8/89 | (2006.01) |
| A61K 8/97 | (2017.01) |
| A61Q 5/00 | (2006.01) |
| A61K 8/67 | (2006.01) |
| A61K 8/98 | (2006.01) |
| A61K 8/64 | (2006.01) |
| A61Q 5/04 | (2006.01) |

(52) U.S. Cl.
CPC ............... *A61K 8/342* (2013.01); *A61K 8/34* (2013.01); *A61K 8/416* (2013.01); *A61K 8/64* (2013.01); *A61K 8/67* (2013.01); *A61K 8/89* (2013.01); *A61K 8/97* (2013.01); *A61K 8/981* (2013.01); *A61Q 5/002* (2013.01); *A61Q 5/04* (2013.01); *A61K 2800/262* (2013.01)

(58) Field of Classification Search
None
See application file for complete search history.

(56) References Cited

U.S. PATENT DOCUMENTS

| 2,942,008 A | * | 6/1960 | Lubowe | ................. A61K 8/922 252/364 |
|---|---|---|---|---|
| 6,153,569 A | | 11/2000 | Halloran | |
| 6,540,989 B2 | * | 4/2003 | Janchitraponvej | ..... A61K 8/345 424/70.1 |
| 7,758,971 B2 | | 7/2010 | Igarashi et al. | |
| 7,964,201 B2 | * | 6/2011 | Bertz | ..................... A61K 8/342 424/401 |
| 8,518,422 B2 | | 8/2013 | Monks et al. | |
| 8,895,034 B2 | | 11/2014 | Bennett | |
| 2003/0103930 A1 | | 6/2003 | Uchida et al. | |
| 2004/0110650 A1 | * | 6/2004 | Siddiqui | .................. A61K 8/66 510/119 |
| 2004/0234491 A1 | * | 11/2004 | Brautigam | ........... A61K 8/8152 424/70.28 |
| 2005/0069516 A1 | * | 3/2005 | Hornby | ..................... A61Q 5/12 424/74 |
| 2008/0112912 A1 | * | 5/2008 | Springob | .................. A61Q 5/00 424/70.12 |
| 2008/0138308 A1 | * | 6/2008 | Belmar | .................. A61K 8/342 424/70.19 |
| 2009/0041710 A1 | * | 2/2009 | Molenda | ............... A61K 8/9789 424/70.12 |
| 2009/0053290 A1 | | 2/2009 | Sand et al. | |
| 2009/0068255 A1 | | 3/2009 | Yu et al. | |
| 2013/0012446 A1 | * | 1/2013 | Sierra-Honigmann | ...................... A61K 8/65 435/68.1 |
| 2014/0246041 A1 | * | 9/2014 | Krueger | ................. A61K 8/466 132/202 |
| 2016/0235851 A1 | * | 8/2016 | Sand | ....................... A61K 33/00 |
| 2020/0206111 A1 | * | 7/2020 | Lee | ......................... A61K 8/416 |

FOREIGN PATENT DOCUMENTS

| EP | 0027730 A2 * | 4/1981 | ............... A61K 8/02 |
|---|---|---|---|
| FR | 2876905 A1 * | 4/2006 | ............... A61Q 5/12 |
| WO | WO-2009074465 A2 * | 6/2009 | ............. A61K 8/922 |
| WO | WO-2015024078 A1 * | 2/2015 | ............. A61K 8/898 |
| WO | WO-2015199753 A1 * | 12/2015 | ............. A61K 33/26 |

* cited by examiner

*Primary Examiner* — Ileana Popa
*Assistant Examiner* — Alissa Prosser
(74) *Attorney, Agent, or Firm* — Frost Brown Todd LLP

(57) ABSTRACT

Disclosed herein are hair care compositions and methods of using same. The compositions may be substantially anhydrous, and optically clear. The hair care compositions, when mixed with water, create an exothermic reaction, for example, when mixed with hair that has been pre-wetted. The mixture with water further causes the composition to become opaque, much like a traditional conditioning agent. The compositions may be left on the wetted hair and subjected to heat for enhanced treatment of the hair.

3 Claims, No Drawings

HAIR CARE COMPOSITIONS AND METHODS OF MAKING AND USING SAME

CROSS-REFERENCE TO RELATED APPLICATIONS

This application claims priority to and benefit of U.S. Provisional Application Ser. No. 62/674,736 filed May 22, 2018, entitled "Hair Care Compositions and Methods of Making and Using Same," the contents of which are incorporated in their entirety for all purposes.

BACKGROUND

While many products are available for providing benefits to the hair and scalp, there remains a need in the art for products that provide improved hair and scalp care, and which may be used to improve one or more of hair appearance, health, and/or manageability and/or overall scalp health. Such need may be particularly profound in individuals exposed to extreme conditions, such as frequent swimming, sun, or chemical treatments, or, in some instances who are prone to scalp conditions such as irritation, itch, flaking, or dandruff. While many products in the art purport to address such needs in the art, improved products are lacking. The instant disclosure addresses one or more of the aforementioned needs in the art.

BRIEF SUMMARY

Disclosed herein are hair care compositions and methods of using same. The compositions may be substantially anhydrous, and optically clear. The hair care compositions, when mixed with water, create an exothermic reaction, for example, when mixed with hair that has been pre-wetted. The mixture with water further causes the composition to become opaque, much like a traditional conditioning agent. The compositions may be left on the wetted hair and subjected to heat for enhanced treatment of the hair.

DETAILED DESCRIPTION

Definitions

Unless otherwise noted, terms are to be understood according to conventional usage by those of ordinary skill in the relevant art. In case of conflict, the present document, including definitions, will control. Preferred methods and materials are described below, although methods and materials similar or equivalent to those described herein may be used in practice or testing of the present invention. All publications, patent applications, patents and other references mentioned herein are incorporated by reference in their entirety. The materials, methods, and examples disclosed herein are illustrative only and not intended to be limiting.

As used herein, the articles including "a" and "an" when used in a claim, are understood to mean one or more of what is claimed or described.

"Apply" or "application" as used in reference to a composition, means to apply or spread the compositions of the present invention onto keratinous fiber such as the hair.

The term "about" or "approximately" means within an acceptable error range for the particular value as determined by one of ordinary skill in the art, which will depend in part on how the value is measured or determined, e.g., the limitations of the measurement system. For example, "about" may mean within 1 or more than 1 standard deviation, per the practice in the art. Alternatively, "about" may mean a range of up to 20%, or up to 10%, or up to 5%, or up to 1% of a given value. Alternatively, particularly with respect to biological systems or processes, the term may mean within an order of magnitude, preferably within 5-fold, and more preferably within 2-fold, of a value. Where particular values are described in the application and claims, unless otherwise stated the term "about" meaning within an acceptable error range for the particular value should be assumed.

For the purposes of the present disclosure, the term "optically clear" is used to define a composition that is transparent (transmitting light without distortion). Which means that the size of the particles in the composition are reduced to a size where they are not observable with optical (visual) means. According to the present invention, "optically clear" is further defined by NTU's (Nephelometric Turbidity Units), which is the unit of measure for the turbidity or haze of a liquid. NTU's range from 0.04 to 1,000 or higher. A more detailed description of this test is described in, for example, U.S. Pat. No. 6,153,569

As used herein, "comprising" means that other steps and other ingredients which do not affect the end result can be added. This term encompasses the terms "consisting of" and "consisting essentially of".

"Leave-on," in reference to compositions, means compositions intended to be applied to and allowed to remain on the keratinous fibers. These leave-on compositions are to be distinguished from rinse-off compositions, which are applied to the hair and subsequently (in a few minutes or less) removed either by washing, rinsing, wiping, or the like. Leave-on compositions exclude rinse-off applications such as shampoos, rinse-off shampoos, facial cleansers, hand cleansers, body wash, or body cleansers. The leave-on compositions may be substantially free of cleansing or detersive surfactants. For example, "leave-on compositions" may be left on the keratinous fibers for at least 15 minutes. For example, leave-on compositions may comprise less than 1% detersive surfactants, less than 0.5% detersive surfactants, or 0% detersive surfactants. The compositions may, however, contain emulsifying, dispersing or other processing surfactants that are not intended to provide any significant cleansing benefits when applied topically to the hair.

"Hair," as used herein, means mammalian hair including scalp hair, facial hair and body hair, particularly on hair on the human head and scalp.

As used herein, "mixtures" is meant to include a simple combination of materials and any compounds that may result from their combination.

As used herein, "molecular weight" or "M.Wt." refers to the weight average molecular weight unless otherwise stated.

As used herein, the terms "include," "includes," and "including," are meant to be non-limiting and are understood to mean "comprise," "comprises," and "comprising," respectively.

The phrase "substantially free of" as used herein, unless otherwise specified means that the composition comprises less than about 5%, preferably less than about 3%, more preferably less than about 1% and most preferably less than about 0.1% of the stated ingredient. The term "free of" as used herein means that the composition comprise 0% of the stated ingredient that is the ingredient has not been added to the composition, however, these ingredients may incidentally form as a byproduct or a reaction product of the other components of the composition.

Disclosed herein are compositions for use on the hair and/or scalp. Applicant has found that, by removing as much water as possible from the disclosed compositions, many benefits may be obtained. For example, in one aspect, by adding water during use, a cream composition from an initially liquid composition can be obtained. During the addition of water during use, it is believed, without intending to be limited by theory, that an exothermic process is initiated, which in turn, enhances penetration and effectiveness of the formula, in particular, the penetration of beneficial components such as vitamins and nutrients into the hair follicle and/or scalp. In other aspects, the disclosed compositions may be provided in a concentrated form. After the addition of water, a thick, rich cream may be formed via manual manipulation. The agitation and/or mixing of the composition during use both produces a cream and further enhances the effectiveness of the product, in that the manual motion used to create the cream massages the product into the scalp and hair. In contrast, products provided initially as a cream may or may not be massaged thoroughly into the hair and onto the scalp, thus precluding maximum effectiveness.

Compositions

Disclosed herein are hair care formulations, in particular, compositions that are substantially clear, and which are substantially anhydrous. The compositions may be in the form of rinse-off or leave-on compositions.

The formulations may comprise, for example, one or more of the following: a vitamin, a humectant, a fatty alcohol, a cationic quaternary ammonium compound, a silicone, an antioxidant, a hydrolyzed protein, an essential oil, a vegetable derived stem cell; and anhydrous alcohol. In one aspect, the hair care formulation may further comprise an enhancer. The permeation enhancer may be used at a concentration of from about 0.005% to about 5%, or about 0.05% to about 0.1%.

In one aspect, the hair care formulations may comprise less than 5% water. In one aspect, the hair care formulation is substantially anhydrous.

In one aspect, a haircare composition comprising an anhydrous alcohol; a fatty alcohol; and a conditioning agent is disclosed, wherein the composition is substantially free of water, or less than about 5% water, or less than about 4% water, or less than about 3% water, or less than about 2% water, or less than about 1% water, or less than about 5% water, or less than about 0.1% water. The haircare composition, in one aspect, is optically clear. The haircare composition, when mixed with water, may form an opaque cream similar to that of a traditional conditioning agent. This may occur when water is added at a percentage of from about 10% to about 20%, or, in certain aspects, about 11%, about 12%, about 13%, about 14%, about 15%, about 16%, about 17%, about 18%, about 19%, about 20%, about 21%, about 22%, about 23%, about 24%, about 25%.

The composition my further include one or more agents as described below, for example, one or more agents selected from a vitamin, a humectant, a silicone, an antioxidant, a hydrolyzed protein; an essential oil; a vegetable derived stem cell, and combinations thereof.

In one aspect, a method of treating hair is disclosed. In one aspect, the method may comprise the steps of a. contacting a composition a substantially anhydrous, optionally clear composition as described herein with the hair of an individual;

b. contacting the composition of step a with a source of water; and c. mixing the composition with water for a period of time sufficient to form an opaque composition.

The mixing step may include the mixing that would occur naturally when one massages the composition into the scalp and hair of an individual, wherein the hair contains some water, for example, after washing or merely wetting of the hair. The mixing step may cause the clear composition to become opaque, much like a conditioning agent as is typical in the art. The formation of the opaque mixed formulation further releases heat—i.e., the reaction is an exothermic reaction, which further adds to the sensorial experience of the treatment, and further improves the penetration and efficacy of one or more active agents contained in the composition. The contacting step a may be carried out for a period of time of from about 30 seconds to about 30 minutes or more. In other aspects, heat may be added following application of the composition (containing water, whether or not supplied by the hair and/or scalp of the individual). The heating step may include use of a hair dryer, and the heat may be in the temperature range of from about 100 to about 150, or at least above 100 degrees, or at least above 110 degrees, or at least above 120 degrees, or at least above 130 degrees.

The method further, in most instances, includes the step of rinsing said composition from the hair of said individual, though in some aspects, a small amount (including trace amounts) of product may be left on the hair and/or scalp of the individual.

In one aspect, the compositions and methods may be used in the context of a chemical hair treatment. For example, in one aspect, the composition may be applied to the hair of an individual following a chemical treatment, for example, a keratin process for straightening or a process for chemically curling hair.

Vitamins

The compositions of the present invention may contain also vitamins and amino acids such as: water soluble vitamins such as vitamin B1, B2, B6 (pyridoxine HCl), B12, ascorbic acid (vitamin C), retinyl palmitate, cobalamin, tocopherol (vitamin E), pantothenic acid, pantothenyl ethyl ether, panthenol, DL-panthenol, dimethiconol panthenol, panthenyl hydroxypropyl steardimonium chloride, biotin, and their derivatives, water soluble amino acids such as asparagine, alanin, indole, glutamic acid and their salts, water insoluble vitamins such as vitamin A, and D, and their derivatives, water insoluble amino acids such as tyrosine, tryptamine, and their salts. In one aspect, the vitamin may be any alcohol soluble vitamin.

The vitamin may be present in an amount of from about 0.0005% to about 10%, or from about 0.005% to about 5%, or from about 0.01% to about 2.5%, or from about 0.05% to about 0.1%, by weight percent, of the composition.

Humectants

The compositions of the present invention may contain a humectant. The humectants herein may be selected from polyhydric alcohols, water soluble alkoxylated nonionic polymers, and mixtures thereof. The humectants, when used herein, may be used at levels of from about 0.005 to about 20%, or from about 0.05% to about 10%, or from about 0.1% to about 0.5%, or from about 0.5% to about 5%, or from about 1.0 to about 2.5%.

Polyhydric alcohols that may be used may include glycerin, for example, PPG-10 methyl glucose ether, sold under the tradename Glucam P-10, methyl gluceth-10, PPG-20, methyl glucose ether, methyl gluceth-20, sorbitol, propylene glycol, butylene glycol, hexylene glycol, ethoxylated glucose, 1,2-hexane diol, hexanetriol, erythritol, trehalose, diglycerin, xylitol, maltitol, maltose, glucose, fructose, sodium chondroitin sulfate, sodium hyaluronate, sodium adenosine phosphate, sodium lactate, pyrrolidone carbonate, glucosamine, cyclodextrin, glycereth-26, sorbitol (70%), propylene glycol, dipropylene glycol, propanediol, and mixtures thereof. In one aspect, the polyhydric alcohol is glycerin.

Water soluble alkoxylated nonionic polymers useful herein include polyethylene glycols and polypropylene glycols having a molecular weight of up to about 1000 such as those with CTFA names PEG-200, PEG-400, PEG-600, PEG-1000, and mixtures thereof.

Fatty Alcohol

The fatty alcohols described herein may include those having from about 14 to about 30 carbon atoms, alternatively from about 16 to about 22 carbon atoms. These fatty alcohols are saturated and can be straight or branched chain alcohols. Nonlimiting examples of fatty alcohols include cetyl alcohol, stearyl alcohol, cetearyl alcohol, myristyl alcohol, lauryl alcohol, behenyl alcohol, and mixtures thereof. The fatty alcohol derivatives and fatty acid derivatives useful herein include alkyl ethers of fatty alcohols, alkoxylated fatty alcohols, alkyl ethers of alkoxylated fatty alcohols, esters of fatty alcohols, fatty acid esters of compounds having esterifiable hydroxy groups, hydroxy-substituted fatty acids, and mixtures thereof. Nonlimiting examples of fatty alcohol derivatives and fatty acid derivatives include materials such as methyl stearyl ether; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through steareth-10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e., a mixture of fatty alcohols containing predominantly cetyl and stearyl alcohol, wherein the numeric designation indicates the number of ethylene glycol moieties present; C16-C30 alkyl ethers of the ceteth, steareth, and ceteareth compounds just described; polyoxyethylene ethers of behenyl alcohol; ethyl stearate, cetyl stearate, cetyl palmitate, stearyl stearate, myristyl myristate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, glyceryl monostearate, glyceryl distearate, glyceryl tristearate, and mixtures thereof. Additional fatty alcohols that may be useful herein include those having from about 14 to about 30 carbon atoms, from about 16 to about 22 carbon atoms. These fatty alcohols may be saturated and can be straight or branched chain alcohols. Exemplary alcohols include, for example, cetyl alcohol, stearyl alcohol, behenyl alcohol, and mixtures thereof. Single compounds of pure fatty alcohols selected from the group of pure cetyl alcohol, stearyl alcohol, and behenyl alcohol may be used. By "pure" herein, what is meant is that the compound has a purity of at least about 90%, at least about 95%. These single compounds of high purity provide good rinsability from the hair when the consumer rinses off the composition. The fatty alcohol may be included in the composition at a level of from about 10% to about 40%, or from about 12% to about 30%, or from about 15 to about 20%, or from about 20% to about 25%, by weight of the composition.

Cationic Quaternary Ammonium Compound

Cationic surfactant, which are generally a quaternary ammonium compound such as ditallow dimethyl ammonium chloride, and fatty alcohols, such as cetyl and stearyl alcohols. Quaternary ammonium compounds useful herein are those having at least one group selected from the group consisting of ester group, amido group, and mixtures thereof. Nonlimiting examples of quaternary ammonium compounds include, for example, di-(alkylcarboxymethyl) hydroxyethyl methyl ammonium methosulfate, and methyl bis-(alkylamidoethyl) 2-hydroxyethyl ammonium methosulfate. Commercially available quaternary ammonium compounds useful herein may include: di-(alkylcarboxymethyl) hydroxyethyl methyl ammonium methosulfate with tradenames Rewoquat V3620 and Rewoquat WE15 both available from Goldschmidt, and with tradenames Dehyquart L80 and Dehyquart F75 both available from Cognis; and methyl bis-(alkylamidoethyl) 2-hydroxyethyl ammonium methosulfate with a tradename Varisoft 222 LT-90 available from Goldschmidt. The compositions may comprise one or more quaternary ammonium salts, for example, cetrimonium chloride, cetrimonium bromide, steartrimonium chloride, behentrimonium chloride, behentrimonium methosulfate, quaternium-91, dicetyl dimonium chloride, distearyldimonium chloride, or a combination thereof. The cationic quaternary ammonium compound may be included in the composition at a level of from about 5% to about 15%, from 5% to about 50%, from 10% to about 40%, or from about 12% to about 30%, or from about 15 to about 20%, or from about 20% to about 25%. In one aspect, the quaternary compounds may be used at a concentration of from about 0.005% to about 15%, from about 0.05% to about 10%, or from about 0.5% to about 5%, or about 7.5% to about 12.5%, by weight of the composition.

Silicone

The compositions may contain a silicone compound, for example, phenyltrimethicone, dimethicone, cyclomethicone, amodimethicone, and combinations thereof. The silicone compounds herein can be used at levels by weight of the composition of from about 0.005% to about 15%, from about 0.05% to about 10%, or from about 0.5% to about 5%, or about 4% to about 6%, by weight of the composition.

Antioxidant

The compositions may contain an antioxidant. As used herein, suitable antioxidants may include green tea extract in glycerin, acai extract, oat extract, white tea extract, black tea extract, an herbal extract, a chamomile extract, or the like. The antioxidant may be included in the composition at a level of from about 0.0005% to about 5%, or from about 0.005% to about 2.5%, or from about 0.05% to about 1%, or from about 0.005% to about 1% by weight of the composition.

Vegetable Derived Stem Cell

In one aspect, the composition may comprise a vegetable derived stem cell or cell extract. These may include, for example, *Rhododentron ferrugineum* leaf cell culture extract, *Vitis vinifera* fruit cell extract, *Malus domestica* fruit cell extract, phytocelltec alp rose (rose stem cells) or extract thereof, vegetable derived stem cells or extract thereof, grape cells or extract thereof, apple cells or extract thereof, or the like. The vegetable derived stem cell may be included in the composition at a level of from about 0.0005% to about 2%, or from about 0.005% to about 1%, or from about 0.05% to about 0.5%, or from about 0.05% to about 0.1% by weight of the composition.

Anhydrous Alcohol

In one aspect, the composition may comprise an anhydrous alcohol, for example cosmetic grade specially denatured alcohol (SDA), for example selected from the group SDA-23, SDA-40 200 proof, and SDA 40B, available from Pharmco-Aaper. In this aspect, the anhydrous alcohol may be included in the composition at a level of from about 40% to about 70%, or from about 50% to about 60% by weight of the composition. The composition may comprise from about 1%, 3%, 5%, 10%, 15%, 20%, 25%, 30%, 35%, 40%, 45%, 50%, 55%, 60%, 65%, 70%, 75%, 80%, 85%, or 90% to about 90%, 85%, 80%, 75%, 70%, 65%, 60%, 55%, 50%, 45%, 40%, 35%, 30%, 25%, 20%, 15%, 10%, or 5% of an anhydrous alcohol. The term "anhydrous" as used herein, unless otherwise specified, refers to those compositions or materials containing less than about 10%, more preferably less than about 5%, even more preferably less than about 3%, even more preferably zero percent, by weight of water. Anhydrous alcohols may include monohydric alcohols, dihydric alcohols, polyhydric alcohols, glycerol, glycols, polyalkylene glycols such as polyethylene glycol, and mixtures thereof, lower aliphatic alcohols such as ethanol, propanol, butanol, isopropanol; diols such as 1,2-propanediol, 1,3-propanediol, butanediol, pentanediol, hexanediol, heptanediol, octanediol, ethylhexanediol, decanediol; and mixtures thereof.

Enhancer. In one aspect, the compositions may comprise an enhancer, for example, the enhancer sold under the tradename Percorium™ by AmperSand such as that described in "Methods and formulations for transdermal administration," PCT/US2014/072239, filed Dec. 23, 2014, also published as US 20160235851, the contents of which are incorporated in its entirety by reference, and which describes a formulation for transdermal delivery of an active agent through the skin, nail or hair follicle of a subject, comprising at least one active agent in an amount effective for treatment of a condition in a subject, 0.5-20% w/w benzyl alcohol, and 25-70% w/w lecithin organogel. The enhancer may be Percorium™ and may be included in the composition at a level of from about 0.0005% to about 5%, or from about 0.005% to about 2.5%, or from about 0.05% to about 1% by weight of the composition.

pH. The pH of the compositions of the present invention vary from about 3.5 to about 6.5. The pH of the compositions can be adjusted using organic acids, such as citric acid, lactic acid, malic acid and succinic acid; or alkaline materials, such as sodium hydroxide or potassium hydroxide. In one aspect, the compositions herein are neutral compositions. In other aspects, the compositions may have a pH in the range of from about 5.0 to about 8.0, or from about 5.5 to about 7.5, more preferably from about 5.5 to about 6.5, wherein the pH is measured at 25° C. Accordingly, the compositions herein may comprise suitable bases and acids to adjust the pH. A suitable base to be used herein is an organic and/or inorganic base. Suitable bases for use herein are the caustic alkalis, such as sodium hydroxide, potassium hydroxide and/or lithium hydroxide, and/or the alkali metal oxides such as, sodium and/or potassium oxide or mixtures thereof. A preferred base is a caustic alkali, more preferably sodium hydroxide and/or potassium hydroxide. Other suitable bases include ammonia, ammonium carbonate, all available carbonate salts such as $K_2CO_3$, $Na_2CO_3$, $CaCO_3$, $MgCO_3$, etc., alkanolamines (e.g., monoethanolamine), urea and urea derivatives, polyamine, etc. Typical levels of such bases, when present, are from about 0.01 wt % to about 5.0 wt %, preferably from about 0.05 wt % to about 3.0 wt %, and more preferably from about 0.1 wt % to about 0.6 wt %, wherein the wt % is relative to the total weight of the composition. The compositions may comprise an acid to adjust the pH to the required level, despite the presence of an acid, if any, the skin cleansing compositions herein will maintain their preferred neutral, pH as described herein above. A suitable acid for use herein is an organic and/or an inorganic acid. A preferred organic acid for use herein has a pKa of less than 6. A suitable organic acid is selected from the group consisting of citric acid, lactic acid, glycolic acid, succinic acid, glutaric acid and adipic acid and a mixture thereof. A mixture of the acids may be commercially available from BASF under the trade name Sokalan® DCS. A suitable inorganic acid is selected from the group consisting of hydrochloric acid, sulfuric acid, phosphoric acid and a mixture thereof. A typical level of such an acid, when present, is from about 0.01 wt % to about 5.0 wt %, preferably from about 0.04 wt % to about 3.0 wt % and more preferably from about 0.05 wt % to about 1.5 wt %, wherein the wt % is relative to the total weight of the composition.

Optional Ingredients

Fragrances, chelating agents, preservatives, colorants and other conventional cosmetic ingredients can also be included at their usual concentrations for use in hair compositions, for example, from about 0.05% to about 2%, or from about 0.5% to about 1.0%

Perfume. The concentrated hair care composition may comprise from about 1% to about 7%, alternatively from about 1.5% to about 6%, and alternatively from about 2% to about 5% perfume, by weight of the concentrated hair care composition. Examples of suitable perfumes may be provided in the CTFA (Cosmetic, Toiletry and Fragrance Association) 1992 International Buyers Guide, published by CFTA Publications and OPD 1993 Chemicals Buyers Directory 80th Annual Edition, published by Schnell Publishing Co. A plurality of perfume components may be present in the concentrated hair care composition.

Hydrolyzed protein. The compositions may contain a hydrolyzed protein such as hydrolyzed silk protein, crosilk liquid (silkworm protein), hydrolyzed vegetable protein, hydrolyzed keratin, hydrolyzed collagen, hydrolyzed wheat protein, or the like. The hydrolyzed protein may be included in the composition at a level of from about 0.0005% to about 2%, or from about 0.005% to about 1.5%, or from about 0.05% to about 1% by weight of the composition.

Essential oil. The compositions may contain one or more essential oils. Exemplary essential oils include moringa oil, manila oil, wheat germ oil, avocado oil, CBD oil, vegetable oil, argan oil, jojoba oil. The essential oil may be included in the composition at a level of from about 0.0005% to about 5%, or from about 0.005% to about 2.5%, or from about 0.05% to about 1.0% by weight of the composition.

In some aspects, the composition may be provided to an individual in the form of a kit. The kit is a package which houses a container which contains the composition, and instructions for using the composition. The kit may optionally also contain one or more additional agents used for hair care. The kit may optionally contain instructions for use. The kit may contain suitable delivery devices, e.g., syringes, and the like, along with instructions for administering the composition. The kit may optionally contain instructions for storage, reconstitution (if applicable), and administration of the composition.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus may be considered to constitute examples of modes for its practice. However, those of skill in the art should, in light of the present disclosure, appreciate that many changes may be made in the specific embodiments that are disclosed and still obtain a like or similar result without departing from the spirit and scope of the invention.

Method of Making

Carefully weigh and add the following material to the MAIN TANK the ingredients as listed above, and mix with constant agitation.

Turn on the mixer and maintain continuous agitation during the mixing process.

Heat the tank to 30-38° C.

Stop heating main tank

Mix thoroughly for 30 minutes while maintaining the temperature of the MAIN TANK between 30-35° C.

Continue to mix the batch for 30 minutes.

Release to be filled or transferred to holding tank or totes.

Method of Using

Five to 15 mL of the disclosed composition is applied to wet or damp hair and scalp. The product is massaged into the scalp and hair for a period of time sufficient to form a cream. In one aspect, the hair and/or scalp is blow dried using heat prior to rinsing. In another aspect, a heat lamp may be used to heat the product applied to the hair and/or scalp. In one aspect, the product may be left on the hair/scalp for about 1 minute, or about 2 minutes, or about 3 minutes or up to 5 minutes or up to 10 minutes or up to 20 minutes, or up to 30 minutes. The product is then rinsed from the hair/scalp with water. The hair/scalp may then be washed/conditioned and styled as usual.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A haircare composition consisting of
   a. from about 50% to about 60% by weight of the composition of anhydrous ethanol;
   b. from about 10% to about 40% by weight of cetyl alcohol;
   c. from about 5% to about 15% by weight of cetrimonium chloride;
   d. panthenol;
   e. pyridoxine HCl;
   f. glycerin;
   g. humectant;
   h. phenyltrimethicone;
   i. one or more-antioxidants selected from green tea extract, acai extract, oat extract, white tea extract, black tea extract, herbal extract, and chamomile extract; and
   j. vitamin b12;
      wherein said composition is optically clear
      wherein said composition is free of added water; and
      wherein said composition is free of detersive surfactants.

2. The haircare composition of claim 1, wherein said composition forms an opaque cream when mixed with water.

3. The haircare composition of claim 2, wherein said composition forms an opaque cream when in water at a percentage of about 10% to about 20% by weight.

\* \* \* \* \*